United States Patent [19]

Mondain-Monval

[11] Patent Number: 4,820,258

[45] Date of Patent: Apr. 11, 1989

[54] RADIOSENSITIZING BIOLOGICAL TISSUES

[75] Inventor: Gérard Mondain-Monval, Paris, France

[73] Assignee: L'Air Liquide, Societe Anonyme Pour L'Etude Et L'Exploitation Des Procedes Georges Claude, Paris, France

[21] Appl. No.: 30,260

[22] Filed: Mar. 24, 1987

[30] Foreign Application Priority Data

Apr. 14, 1986 [FR] France ................................ 86 05277

[51] Int. Cl.$^4$ ............................................... A61N 5/10
[52] U.S. Cl. ....................................................... 600/1
[58] Field of Search ........................... 128/1.1, 1.2, 910

[56] References Cited

U.S. PATENT DOCUMENTS

| 4,151,843 | 5/1979 | Brekke et al. | 128/910 |
| 4,202,323 | 5/1980 | Zwerg et al. | 128/1.1 |
| 4,248,218 | 2/1981 | Fischer | 128/910 |
| 4,331,142 | 5/1982 | Degan | 128/207.15 |
| 4,446,861 | 5/1984 | Tada | 128/910 |
| 4,454,879 | 6/1984 | Peterson | 128/203.12 |
| 4,580,561 | 4/1986 | Williamson | 128/1.2 |

FOREIGN PATENT DOCUMENTS 1396772  6/1975  United Kingdom .

*Primary Examiner*—Francis Jaworski
*Assistant Examiner*—John C. Hanley
*Attorney, Agent, or Firm*—Browdy and Neimark

[57] ABSTRACT

A gaseous mixture comprising oxygen, nitrous oxide, and an optional inert gas, is useful for radiosensitizing tissues in radiotherapy, particularly for treatment of cancer.

8 Claims, No Drawings

RADIOSENSITIZING BIOLOGICAL TISSUES

FIELD OF INVENTION

This invention relates to a product for radiosensitizing of biological tissues in radiotherapy.

BACKGROUND OF THE INVENTION

It is known that well "oxygenated" cells are more sensitive to radiation, and that anoxia reduces radiosentitivity of cells. Tumoral cells often are poorly "oxygenated," and therefore are not very sensitive to therapeutic radiations.

Hyperbaric oxygen therapy makes it possible to increase oxygenation of tumoral cells and consequently to make them more vulnerable to radiation, and thus to improve the effectiveness of a therapeutic irradiation. Therefore, a therapy combining radiotherapy and hyperbaric oxygen therapy has been developed, according to which the patient is placed under oxygen in a single-person hyperbaric chamber transparent to radiation and placed under a radiation generator (X or gamma-cobalt).

The development of this therapy is slowed down by the cost and awkwardness of implementation and of the equipment required: hyperbaric chamber, protocol and remote monitoring of the patient placed in the chamber and under irradiation, compression and decompression process, safety precautions because of the use of pure oxygen in the chamber, etc.

To increase the oxygenation of the cells without using hyperbaric oxygen therapy, "normobaric" oxygen therapy was proposed. This therapy comprising in inhalation by the patient at ambient pressure of superoxygenated air, even of pure oxygen, already represented a first improvement, but makes it possible to increase only slightly the amount of oxygen available in the blood and tissues.

Also, a more effective means of radiosentitizing the cells to be treated by radiotherapy was sought.

SUMMARY OF THE INVENTION

A gaseous mixture containing at least oxygen and nitrous oxide makes it possible to obtain this effect in a very satisfactory way.

Nitrous oxide is already known as a product that can be used particularly in the therapeutic field. British Pat. No. 1,396,722 refers to the analgesic properties that it manifests and mentions the anesthetic action of mixtures of nitrous oxide, carbon dioxide and oxygen.

A new function has been discovered of a gaseous mixture containing nitrous oxide and corresponding to a role of selective or differential radiosensitizing between healthy and tumoral cell, lipid nerve cells and protein cellular membranes, having no connection with the known analgesic and anesthetic functions.

The radiosensitizing product is inhaled by the patient subjected to radiotherapy. This new use of nitrous oxide does not pose any particular problem for the medical staff. Actually, the latter currently uses nitrous oxide in anesthesia and analgesia, and consequently has a perfect knowledge of it on the physiological, safety, equipment and use technique levels.

The interest of a product for radiosenstitizing of tissues comprising of a gaseous mixture containing at least about 50% by volume of nitrous oxide, preferably about 50 to 80% by volume, and at least about 20% by volume of oxygen has been evaluated.

The product for radiosensitizing of biological tissues can be in the form of a binary mixture comprising of oxygen and nitrous oxide prepared either in advance by premixing or prepared for immediate use by means of a nitrous oxide-oxygen mixer by a safety mixer which delivers a gaseous mixture whose oxygen content is at least about 20% by volume.

The procuct for radiosensitizing of biological tissues can also be in the form of a ternary mixture consisting of oxygen, nitrous oxide and the complement to 100 by volume by an inert gas selected from nitrogen, argon, krypton, xenon and helium.

The two types of binary and ternary mixtures can be prepackaged under pressures compatible with maintaining the mixtures in gaseous form.

Administration of the gas mixture containing nitrous oxide is performed by inhalation with simple, inexpensive equipment, for example, of the mask and intubation probe type.

The patient is made to breathe the radiosensitizing product before irradiation treatment, for a period of 15 to 30 minutes to achieve the saturation of the biological tissues.

The different tissues are more or less rapidly saturated or desaturated with nitrous oxide. The tissues can be diagrammatically classified into three main catagories according to their saturation-desaturation constant. The tissues of the first category have a time constant on the order of 5 minutes, for the second category, the time constant is on the order of 15 minutes, and for the third category, this constant reaches the order of an hour.

This "time" parameter can be profitably used as follows: for example, after an hour of inhalation of a gas mixture rich in nitrous oxide, i.e., containing more than 50% of this gas, it can be considered that the organism is saturated. If inhalation of nitrous oxide is interrupted, after 5 minutes it can be considered that the first category of tissues has eliminated the nitrous oxide and consequently it is possible to proceed to an irradiation. These tissues no longer containing nitrous oxide will be less vulnerable, while the tissues of the 2nd and 3rd category still containing nitrous oxide will be radiosensitized and destroyed by radiation. This example shows the differential or selective effect which the use of nitrous oxide makes it possible to obtain in this application, in particular in the treatment of cancers by radiotherapy.

Further, the differentiation factor also results fom the solubility of the nitrous oxide depending on the type of healthy or tumoral, lipid or protein cell tissues.

An irradiation, started after 30 minutes stoppage of nitrous oxide inhalation, is selectively effective on tissues of the third category.

Inhalation of the radiosensitizing product can be continued during irradiation when it is desired to obtain a strong concentration of nitrous oxide, either in the case of intense preoperative irradiation or more generally in the case where the irradiation zone can be delimited.

DETAILED DESCRIPTION OF THE INVENTION

The radiosensitizing effect of inhalation of a mixture of nitrous oxide and oxygen was shown on batches of healthy mice. The effect of the irradiation was checked on the entire animal's inhaling a nonhypoxiant mixture of nitrous oxide and oxgyen ($N_2O$-$O_2$). The irradiation was delivered by a cobalt 60 source. The mice were placed in a box transparent to radiation, compartmented into 30 small cells each pierced with ventilation orifices on the back face. The device was placed 1 meter from the source in the irradiation field. To assure inhalation of the mixture to be tested, the box was hermetically sealed in a thin plastic bag and ventilated at 5 lit/min by the gas mixture which was rejected into an evacuation chimney. In all the tests, exposure of the mice to a given mixture always started 30 minutes before starting of the irradiation. The result was judged by the mortality rate during the first 30 days.

TABLE

| Series | Nature of Mixture | Irradiation | | | | Died in 30 days | | Test No. |
|---|---|---|---|---|---|---|---|---|
| | | No of Mice | Dose Gy | Intensity Gy/min | Period min | No. | Avg. Period Days | |
| I | Air Controls | 30 a | 8,5 | 0,65 | 13,08 | 23 | 12,1 | 1 |
| | | 30 a | 8,0 | 0,65 | 12,30 | 15 | 15,3 | 2 |
| | | 30 a | 7,5 | 0,65 | 11,29 | 5 | 13,3 | 3 |
| | $N_2O$ 76% $O_2$ 24% | 30 a | 8,0 | 0,65 | 12,30 | 17 | 13,7 | 4 |
| | $N_2O$ 76% $O_2$ 24% | 30 a | 8,5 | 0,65 | 13,08 | 28 | 11,5 | 5 |
| | | 30 a | 8,0 | 0,65 | 12,30 | 23 | 13,0 | 6 |
| | | 30 a | 7,5 | 0,65 | 11,29 | 14 | 13,0 | 7 |
| II | Air Controls | 30 b | 9,0 | 0,63 | 14,29 | 20 | 15,2 | 8 |
| | | 30 b | 8,5 | 0,63 | 13,49 | 9 | 15,4 | 9 |
| | | 30 b | 8,0 | 0,63 | 12,70 | 6 | 14,5 | 10 |
| | | 30 b | 7,5 | 0,63 | 11,90 | 3 | 22,3 | 11 |
| | $N_2O$ 76% $O_2$ 24% | 30 b | 8,5 | 0,63 | 13,49 | 26 | 14,0 | 12 |
| | | 30 b | 8,0 | 0,63 | 12,70 | 23 | 14,1 | 13 |
| | | 30 b | 7,5 | 0,63 | 11,90 | 13 | 15,3 | 14 |
| III | Air Controls | 30 b | 7,5 | 0,61 | 12,30 | 7 | 14,4 | 15 |
| | $N_2O$ 76% $O_2$ 24% | 30 b | 7,5 | 0,61 | 12,30 | 12 | 13,75 | 16 |
| IV | Air Controls | 30 b | 8,5 | 0,59 | 14,41 | 5 | 14,0 | 17 |
| | | 30 b | 8,0 | 0,59 | 13,56 | 4 | 12,1 | 18 |
| | $N_2O$ 76% $O_2$ 24% | 30 b | 8,5 | 0,59 | 14,41 | 27 | 13,8 | 19 |
| | | 30 b | 8,0 | 0,59 | 13,56 | 17 | 12,5 | 20 | a: Female albino mice, stock 17 of the Curie Institute, Age: 4 months, weight: 22 to 24 g.
b: Male mice, stock CD1, production V.A.F. of Charles River, Age: 3 months, weight: 25 to 30 g.
Gy: Gray irradiation unit.

In this table, the comparison between isodose tests in air and in the $N_2O/O_2$ mixture shows that in all cases the inhalation of nitrous oxide causes a radiosensitizing.

More precisely, the first series of tests gives the lethal does at 50% in 30 days, $DL_{50} \pm 2$ 0−, following 8.10±0.15 Gy in air 7.55±0.15 Gy in the $N_2O/O_2$ mixture The difference is very significant $p < 0.001$.

The second difference also gave 8.60±0.15 l Gy in air 7.60±0.15 Gy in the $NO/O_2$ mixture, the difference is also very significant $p < 0.001$.

The two last series of tests served to confirm the first results and it was found that these results are very comparable.

Thus, very significantly ($p < 0.001$) inhalation of a mixture of 76% $N_2O$/24% $O_2$ makes the toxicity of the irratiation, under the test conditions about 10% stronger, in the presence of nitrous oxide.

This radiosensitizing effect of nitrous oxide can be used to increase the effectiveness of the radiotherapy.

The foregoing description of the preferred embodiments will so fully reveal the general nature of the invention that others can, by applying current knowledge, readily modify and/or adapt for various applications such specific embodiments without departing from the generic concept. Such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for delivering radiation to target tissue of a patient undergoing cancer radiotherapy, comprising the steps of:

administering a nonhypoxic gaseous mixture comprising at least about 50% by volume of nitrous oxide to a patient by inhalation until at least some of said patient's biological tissues are saturated with nitrous oxide;

discontinuing administration of said gaseous mixture; then, exposing said target tissue to radiation from a source maintained external to said patient's body after any saturated biological tissues of said patient which eliminate nitrous oxide faster than said target tissue become desaturated with respect to nitrous oxide.

2. The method of claim 1 wherein the gaseous mixture contains from about 50 to 80% by volume of nitrous oxide.

3. The method of claim 1 wherein the gaseous mixture contains at least about 20% by volume of oxygen.

4. The method of claim 1 wherein the gaseous mixture comprises oxygen, nitrous oxide, and an inert gas.

5. The method of claim 4 wherein the inert gas is selected from the group consisting of nitrogen, argon, krypton, xenon, and helium.

6. The method of claim 1 wherein the gaseous mixture is administered for about 15 to about 30 minutes.

7. The method of claim 1 wherein the gaseous mixture is supplied under pressures compatible with maintaining the mixture in a gaseous form.

8. The method of claim 1 wherein the gaseous mixture is obtained by mixing nitrous oxide with oxygen immediately prior to use to obtain a gaseous mixture containing at least 20% by volume of oxygen.

* * * * *